United States Patent [19]

Margetson

[11] 4,302,849
[45] Dec. 1, 1981

[54] ARM SUPPORT DEVICE

[76] Inventor: Desmond W. Margetson, 515 W. 122nd St., New York, N.Y. 10027

[21] Appl. No.: 116,462

[22] Filed: Jan. 29, 1980

[51] Int. Cl.³ ........................... A61F 5/02; A41B 1/00
[52] U.S. Cl. .............................................. 2/115; 2/45
[58] Field of Search ...................... 2/115, 102, 44, 45, 2/16, 17; 128/87

[56] References Cited
U.S. PATENT DOCUMENTS 645,488  3/1900  Osgood ................................... 2/115
945,139  1/1910  Roland ..................................... 2/45
2,163,654  6/1939  Ziegler et al. ........................... 2/115

Primary Examiner—Doris L. Troutman
Attorney, Agent, or Firm—Hammond & Littell, Weissenberger and Muserlian

[57] ABSTRACT

This invention relates to an improved device for supporting arms. More particularly, this invention relates to an improved device to be worn by runners to support arms and to guide arm movements so as to increase running efficiency.

8 Claims, 2 Drawing Figures

U.S. Patent  Dec. 1, 1981  4,302,849
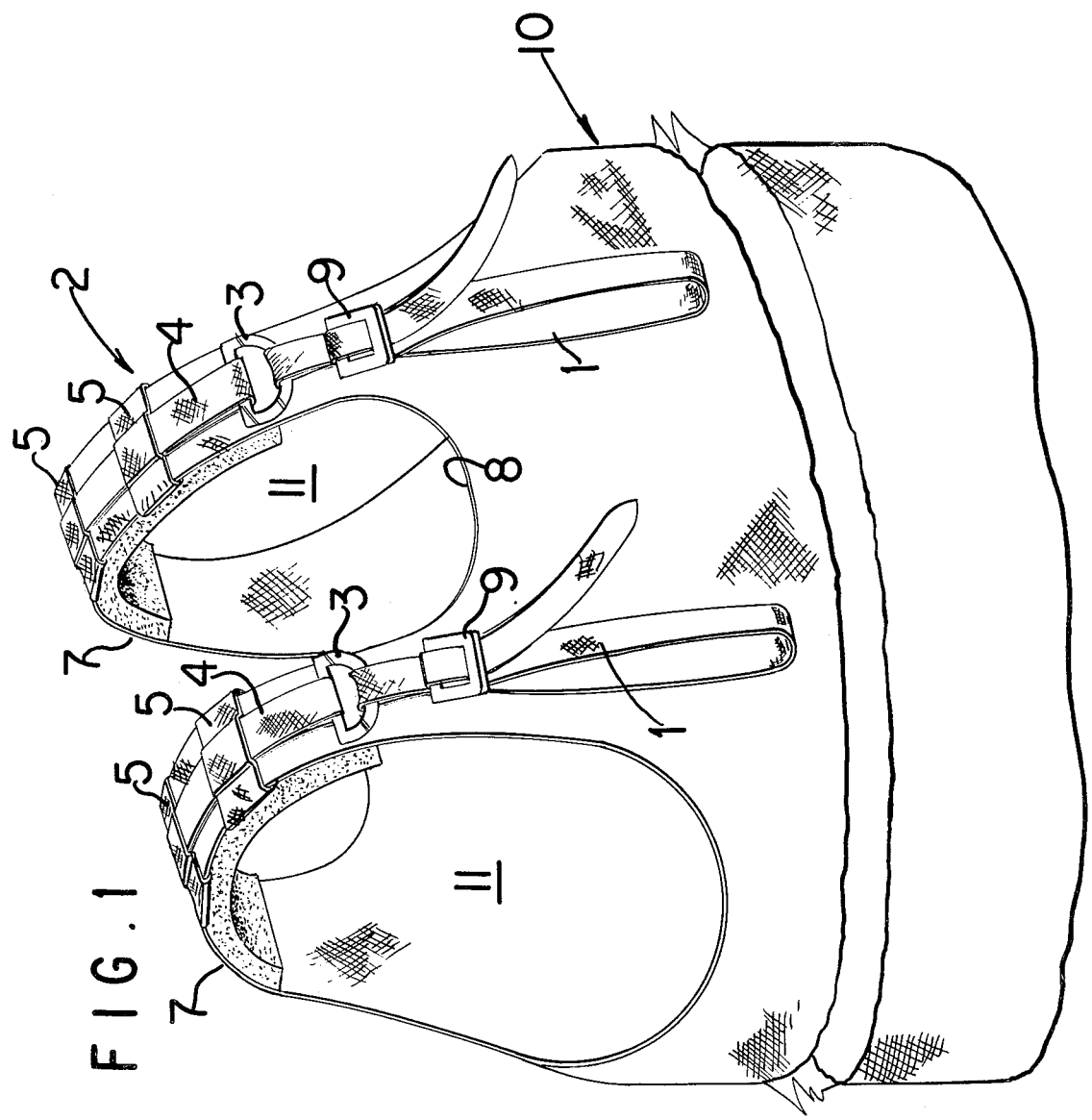

ARM SUPPORT DEVICE

BACKGROUND OF THE INVENTION

Running, particularly jogging, has become a widespread phenomenon. With the onset of this phenomenon, more attention has been paid to the mechanics of and equipment for running. For example, significant developments and improvements have been made during the past five to ten years with regard to running shoes, lightweight and breathable shirts and shorts, as well as lightweight and protective outer gear.

In the typical running motion, the arms of an individual runner alternately swing back and forth. With regard to most runners, particularly recreational runners, the arms do not swing in relaxed, perfect synchronization with legs and respiratory system. Inefficient expenditure of energy is a result; more particularly, the arms themselves tend to become quite tired and to lose suppleness. In fact, general fatigue results from this situation because arm muscles must always be tense to maintain the hands in an elevated position. This leads to a build-up of lactic acid in the muscles and bloodstream that drains oxygen from the bloodstream to convert it to glycogen. Fatigue is the primary problem when long distances are run.

To solve the problems of tired arms as well as general fatigue, a device was developed to allow the arms to swing naturally while running, without the usual tension in the biceps, deltoids, shoulder and chest interface muscles. The device developed consisted of a shirt having hanging therefrom two strap loops, one for each arm. The strap loops were intended to confine the motion of each swinging arm to a more natural, continuous motion close to the body as well as to provide support for each arm, in effect transferring the tension of the arms to the strap loops. Another advantage of this device was that runners who used the shirt tended thereafter to swing their arms in a more natural motion when the shirt wasn't used. The natural motion of arms, when allowed to swing automatically, is continuous and somewhat elliptical in path.

In the device developed, each strap loop was attached by stitches, rivets, and the like, directly to a point adjacent to the respective side of the neck opening. However, a significant difficulty with this arrangement was that the point of attachment tended to tear or separate, often unexpectedly, after short periods of use. Also, the points of attachment could be uncomfortable, and, since the strap loops were integrally attached to the shirts, the shirts were not readily washable in standard washing machines. Furthermore, the shirts were not versatile because they did not permit the runner the option of attaching or removing the straps.

OBJECTS OF THE INVENTION

It is an object of this invention to provide an improved device to forestall fatigue in runners, thereby contributing to development by simultaneously improving the levels of relaxation, coordination, and pleasure.

It is also an object of this invention to provide an improved device to support the arms of runners.

It is further an object of this invention to provide an improved method for attaching strap loops to a shirt to be used for running.

These and other objects of the invention will become more apparent in a discussion below.

BRIEF DESCRIPTION OF THE DRAWINGS

FIG. 1 represents a perspective view of an embodiment of the invention.

FIG. 2 represents a close-up view of means to attach strap loops to an upper body covering according to the invention.

DETAILED DESCRIPTION OF THE INVENTION

Applicant has surprisingly found that adjustable strap loops to support arms and to guide the motion of arms can be effectively attached to the upper portion of an upper body covering. According to the invention, each strap loop is looped around one side of a ring, preferably a D-ring, or a similar mechanical device, which is part of an attachment means. The other side of the ring is connected to an attachment member, i.e., a fitting, which is in turn affixed to the upper body covering by two or more cross-members, said cross-members being reinforced on the underside of the upper body covering. The attachment means are located on the upper portion of the upper body covering, preferably adjacent to a neck opening. This arrangement has the effect of minimizing friction and loading the interface strap loop in tension only.

The upper body covering can be comprised of any suitable fabric, the basic criterion being that the fabric be sufficiently substantial to withstand the loads transmitted from the various fitting members at the point of attachment. Many of the fabrics presently employed for running gear could be used, such as, for example, fabrics comprised of cotton, rayon, nylon, wool, or mixtures thereof. A typical suitable fabric might be comprised of from 20% to 50% by weight of cotton and from 50% to 80% by weight of rayon.

The straps themselves are generally comprised of somewhat more durable material. For example, the straps may be comprised of woven polyester, woven polyethylene, or some other such woven or non-woven synthetic material. Preferably the strap loops are comprised of polypropylene, which is economical to use and is resistant to static electricity build-up. In a preferred embodiment, each strap loop will have a mechanism such as a buckle or other adjustable slide or fastener, for adjusting the length of the loop according to the runner's preference. Strap loop will generally be adjusted to the height of the hands while running, and runners vary widely in this respect.

The ring or other suitable mechanism which connects each strap loop and the attachment means can be comprised of a rigid material such as metal or a thermosetting polymeric material. Preferably a steel D-ring is used to minimize friction and to allow the strap loops to swing freely.

The attachment means member, cross-members and reinforcement, can be comprised of any suitable material which is capable of being sewn, stitched, riveted, glued, or otherwise affixed to the upper body covering. Suitable such materials would include fabric compositions comprising woven cotton, rayon, nylon, or mixtures thereof, or even a woven or non-woven polymeric material.

The attachment means cross-members are, as mentioned above, reinforced on the underside, i.e., inside of the upper body covering. Such reinforcement can be effected by, where feasible, folding under either or both of the ends of the cross-members or by positioning a suitable substrate beneath the cross-members. If the cross-members are stitched to the upper body covering, the stitching should also catch the reinforcement. Regardless of whichever technique is used to provide reinforcement, care should be taken to see that the overall attachment means is flexible and comfortable to the runner.

Auxiliary cushioned pads may be inserted or positioned under the attachment means to distribute load over a wider area and to increase comfort. Such pads may be comprised of rubber, foam rubber, or another suitable material. Examples of such materials include polyurethane foam and sponge rubber.

The invention can perhaps be best appreciated by making reference to the figures. In FIGS. 1, and 2, strap loops 1 are connected to the attachment means 2 by ring 3. Attachment means 2 also comprises attachment member 4 as well as cross-members 5. Cross-members 5 are sewn to upper body covering 6 at straps 7 adjacent to neck opening 8. In this embodiment of the invention, each end of each cross-member 5 is folded under almost one-half of the width of the strap 7 to provide reinforcement when the attachment means is sewn to the upper body covering. One end of attachment member 4 is sewn under to secure ring 3.

The length of each strap can be adjusted by buckle 9.

In the embodiment represented by the FIG. 1, upper body covering 10 represents a typical sleeveless "tank top" running shirt having armholes 11 and body opening 12. However, the attachment means 2 could also be similarly attached to any other upper body covering used for running, such as a shirt, sweatshirt, running jacket, or the like.

The strap loops 1 will typically be from about 0.5 to 3 inches, preferably about 1 to 2 inches, wide and will be long enough to hang from about 8 to 24 inches, preferably from about 12 to 18 inches, from the connecting ring 3.

The attachment member 4 and cross-members 5 can each be from about 0.5 to 3 inches, preferably about 0.75 to 2 inches, wide. Attachment member 4, in position, can be from about 2 to 8 inches, preferably from about 2.5 to 6 inches, long, and each cross-member 5 will be, in position, from about 1.5 to 4 inches, preferably from about 2 to 3 inches, long. Attachment member 4 should be long enough to allow each strap loop 1 to swing from a point well below the runner's collarbones.

The ring 3 will have an inside diameter large enough to cooperate with the strap loops 1 and attachment member 4. The inside diameter of the ring 3 will be from about 0.5 to 4 inches, preferably from about 1 to 2 inches, and the thickness of the ring 3 itself will be from about 0.125 to 0.25 inches. In an especially preferred embodiment, ring 3 is a steel D-ring having an inside dimension on the flat side of about 1 inch.

The preceding specific embodiments are illustrative of the practice of the invention. It is to be understood, however, that other expedients known to those skilled in the art or disclosed herein, may be employed without departing from the spirit of the invention or the scope of the appended claims.

I claim:

1. An upper body covering for running comprising a fabric device having two armholes, a bottom opening, a neck opening, and two strap loops, one end of each strap loop being attached to the upper body covering at a point laterally adjacent to said neck opening by an attachment means affixed to the upper body covering said attachment means comprising a ring onto which the strap loop is looped, a member to which the ring is secured, and two or more cross-members sewn to the upper body covering the cross-members being reinforced on the underside of the upper body covering.

2. The upper body covering of claim 1 wherein each strap loop has a buckle or adjustable slide or fastener to adjust the length of the loop.

3. The upper body covering of claim 1 wherein the strap loops are comprised of woven polypropylene.

4. The upper body of claim 1 wherein the fabric of the covering is selected from the group consisting of cotton, polyester, polyethylene, nylon, rayon, and mixtures thereof.

5. The upper body covering of claim 1 wherein the cross-members are folded under to provide reinforcement.

6. The upper body covering of claim 1 wherein cushioned pads are affixed under the attachment means.

7. The upper body covering of claim 1 wherein the covering comprises a tank top and the attachment means are affixed to the straps of the tank top.

8. The upper body covering of claim 7 wherein cushioned pads are affixed under the straps.

* * * * *